United States Patent
Hupfield et al.

(10) Patent No.: US 9,249,164 B2
(45) Date of Patent: Feb. 2, 2016

(54) PROCESS FOR PREPARING AN ACRYLOYLOXYSILANE

(76) Inventors: Peter Cheshire Hupfield, Trevaughan (GB); Xiaobing Zhou, Midland, MI (US)

(*) Notice: Subject to any disclaimer, the term of this patent is extended or adjusted under 35 U.S.C. 154(b) by 241 days.

(21) Appl. No.: 13/825,633

(22) PCT Filed: Sep. 20, 2011

(86) PCT No.: PCT/US2011/052331
§ 371 (c)(1),
(2), (4) Date: Mar. 22, 2013

(87) PCT Pub. No.: WO2012/050761
PCT Pub. Date: Apr. 19, 2012

(65) Prior Publication Data
US 2013/0184482 A1      Jul. 18, 2013

Related U.S. Application Data

(60) Provisional application No. 61/388,079, filed on Sep. 30, 2010.

(51) Int. Cl.
C07F 7/00 (2006.01)
C07F 7/02 (2006.01)
C07F 7/18 (2006.01)
C07F 7/20 (2006.01)

(52) U.S. Cl.
CPC ............... *C07F 7/025* (2013.01); *C07F 7/1892* (2013.01); *C07F 7/20* (2013.01)

(58) Field of Classification Search
CPC .......................................................... C07F 7/08
USPC .......................................................... 556/444
See application file for complete search history.

(56) References Cited

U.S. PATENT DOCUMENTS

| | | | |
|---|---|---|---|
| 4,946,977 A | 8/1990 | Bernhardt et al. | |
| 5,117,027 A | 5/1992 | Bernhardt et al. | |
| 6,815,554 B2 | 11/2004 | Pfeiffer et al. | |
| 6,841,694 B2 | 1/2005 | Pfeiffer | |
| 7,262,312 B2 | 8/2007 | Sheridan et al. | |
| 2007/0032673 A1* | 2/2007 | Sheridan | C07F 7/1892 556/466 |

FOREIGN PATENT DOCUMENTS

| CN | 101307069 A | 11/2008 |
|---|---|---|
| WO | 2005103061 | 11/2005 |
| WO | 2007018997 | 2/2007 |

OTHER PUBLICATIONS

Freedman, H.H., "Industrial Applications of Phase Transfer Catalysis (PTC): Past, Present and Future", Pure & Appl. Chem. 1986, 58(6), 857.

Stefan Altmann et al.: "The Hydrolysis/Condensation Behaviour of Methacryloyloxyalkylfunctional Alkoxysilanes: Structure-Reactivity Relations", Monatshefte Fur Chemie, Springer Verlag Wien, AT, vol. 134, Jun. 12, 2003, pp. 1081-1092.

Voronkov, M. G. et al.: "BIS/trialkylsilyl/Methyl Alkane- and Alkene-dioates", Journal of General Chemistry USSR, Consultants Bureau, New York, NY, US, vol. 55, No. 10, Jan. 1, 1985, p. 2046.

* cited by examiner

*Primary Examiner* — Porfirio Nazario Gonzalez
*Assistant Examiner* — Kofi Adzamli
(74) *Attorney, Agent, or Firm* — Matthew T. Fewkes

(57) ABSTRACT

A process for preparing an acryloyloxysilane, the process comprising reacting a metal salt of a carboxylic acid having the formula $[CR^2{}_2{=}CR^1COO^-]_a M^{a+}$ (I), with a haloorganoalkoxysilane having the formula $XR^3Si(OR^4)_n R^5{}_{3-n}$ (II) in the presence of mineral spirits and a phase transfer catalyst at a temperature of from 50 to 160° C. to form a mixture comprising an acryloyloxysilane and a metal halide having the formula $M^{a+}X^-{}_a$ (III), wherein $R^1$ is H or $C_1$-$C_6$ hydrocarbyl, each $R^2$ is independently $R^1$ or $[COO^-]_a M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ Q hydrocarbyl, each $R^5$ is independently $R^1$ and n is an integer from 1 to 3.

20 Claims, No Drawings

PROCESS FOR PREPARING AN ACRYLOYLOXYSILANE

CROSS REFERENCE TO RELATED APPLICATIONS

This application is a U.S. national stage filing under 35 U.S.C. §371 of PCT Application No. PCT/US11/052331 filed on Sep. 20, 2011, currently pending, which claims the benefit of U.S. Provisional Patent Application No. 61/388,079 filed Sep. 30, 2010 under 35 U.S.C. §119 (e). PCT Application No. PCT/US11/052331 and U.S. Provisional Patent Application No. 61/388,079 are hereby incorporated by reference.

FIELD OF THE INVENTION

The present invention relates to a process for preparing an acryloyloxysilane comprising reacting a metal salt of an unsaturated carboxylic acid with a haloorganoalkoxysilane, in the presence of mineral spirits and a phase-transfer catalyst to form a mixture comprising a metal halide and an acryloyloxysilane, and removing at least a portion of the metal halide from the mixture.

The present invention also relates to a process of purifying an acryloyloxysilane, the process comprising washing a mixture comprising an acryloyloxysilane, a first metal halide, and a non-polar solvent with a solution comprising water and, optionally, a second metal halide, to produce an organic phase comprising the acryloyloxysilane and an aqueous phase comprising at least a portion of the first metal halide.

BACKGROUND OF THE INVENTION

Unsaturated organoalkoxysilanes containing an acryloyloxy group, such as 3-acryloyloxypropyltriethoxysilane, have been produced by the nucleophilic substitution reaction of a haloorganoalkoxysilane with a metal salt of an unsaturated carboxylic acid, such as sodium acrylate, in the presence of a suitable phase-transfer catalyst. In addition to the desired silane product, this process produces a metal halide precipitate as a by-product, which is unwanted in the silane product and must be removed.

A portion of the metal halide precipitate has a fine particle size that does not settle into a distinct layer making decanting the product from the precipitate difficult on a commercial scale. In addition, washing with water is not practiced to avoid hydrolysis of the silane and formation of dispersions that are hard to separate. Thus, the metal halide is typically removed by filtration. However, to filter the fine particle size and large amount of the metal halide precipitate requires significant time, so filtration is a significant bottleneck in commercial scale production.

Therefore, there is a need for a process for producing an acryloyloxysilane that produces a metal halide by-product precipitate that is more easily removed from the organoalkoxysilane containing an acryloyloxy group. There is also a need for a new process to quickly remove a metal halide from a mixture of an acryloyloxysilane and the metal halide.

BRIEF SUMMARY OF THE INVENTION

The first process of the present invention is directed to a process for preparing an acryloyloxysilane comprising reacting a metal salt of a carboxylic acid having the formula $[CR^2_2=CR^1COO^-]_aM^{a+}$ (I), with a haloorganoalkoxysilane having the formula $XR^3Si(OR^4)_nR^5_{3-n}$ (II) in the presence of mineral spirits and a phase transfer catalyst at a temperature of from 50 to 160° C. to form a mixture comprising an acryloyloxysilane and a metal halide having the formula $M^{a+}X^-_a$ (III), wherein $R^1$ is H or $C_1$-$C_6$ hydrocarbyl, each $R^2$ is independently $R^1$ or $[COO^-]_aM^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

The first processes of the present invention produces an acryloyloxysilane. Further, the first process of the present invention produces a coarse metal halide precipitate that requires less time to filter and that separates quickly from the acryloyloxysilane forming a distinct layer enabling efficient decanting of the acryloyloxysilane from the metal halide.

The second process of the present invention is directed to a process of purifying an acryloyloxysilane comprising washing a mixture comprising an acryloyloxysilane, a first metal halide, and a non-polar solvent with a solution comprising water and, optionally, a second metal halide, to produce an organic phase comprising the acryloyloxysilane and an aqueous phase comprising at least a portion of the first metal halide.

The second process of the present invention provides a new process for the quick separation of a metal halide from a mixture comprising an acryloyloxysilane and a metal halide. Furthermore, the second process of the invention provides for the washing of an acryloyloxysilane without significant hydrolysis or formation of a stable dispersion.

The acryloyloxysilane of the first and second processes of the invention may be used as a coupling agent for unsaturated resin or polymer systems, an adhesion promoter at organic-inorganic interfaces, and as a surface modifier.

DETAILED DESCRIPTION OF THE INVENTION

The first process of the invention is a process for preparing an acryloyloxysilane, the process comprising: reacting a metal salt of a carboxylic acid having the formula $[CR^2_2=CR^1COO^-]_aM^{a+}$ (I), with a haloorganoalkoxysilane having the formula $XR^3Si(OR^4)_nR^5_{3-n}$ (II) in the presence of mineral spirits and a phase transfer catalyst at a temperature of from 50 to 160° C. to form a mixture comprising an acryloyloxysilane and a metal halide having the formula $M^{a+}X^-_a$ (III), wherein $R^1$ is H or $C_1$-$C_6$ hydrocarbyl, each $R^2$ is independently $R^1$ or $[COO^-]_aM^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

The metal salt of an unsaturated carboxylic acid has the formula $[CR^2_2=CR^1COO^-]_aM^{a+}$ (I), wherein $R^1$ is H or $C_1$-$C_6$ hydrocarbyl, each $R^2$ is independently $R^1$ or $[COO^-]_a M^{a+}$, each $M^{a+}$ is an alkali metal cation or alkaline earth metal cation, and a is 1 or 2. Examples of alkali metal or alkaline earth metal cations represented by $M^{a+}$ include $Li^+$, $Na^+$, $K^+$, $Mg^{2+}$, and $Ca^{2+}$. In one embodiment, $M^{a+}$ is $Na^+$ or $K^+$.

The hydrocarbyl groups represented by $R^1$ and $R^2$ typically have from 1 to 6 carbon atoms, alternatively from 1 to 4 carbon atoms, alternatively from 1 to 3 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl.

Examples of the metal salt of an unsaturated carboxylic acid include, but are not limited to, sodium acrylate, sodium methacrylate, sodium ethacrylate (i.e., sodium 2-methylenebutanoate), sodium crotonate, sodium isocrotonate, sodium sorbate, potassium acrylate, potassium methacrylate, potassium ethacrylate (i.e., potassium 2-methylenebutanoate), potassium crotonate, potassium isocrotonate, potassium sorbate, magnesium acrylate, magnesium methacrylate, magnesium ethacrylate, magnesium crotonate, magnesium isocrotonate, magnesium sorbate, calcium acrylate, calcium methacrylate, calcium ethacrylate, calcium crotonate, calcium isocrotonate, and calcium sorbate, monosodium fumarate, disodium fumarate, monosodium maleate, disodium maleate, monosodium itaconate, disodium itaconate, monopotassium fumarate, dipotassium fumarate, monopotassium maleate, dipotassium maleate, monopotassium itaconate, dipotassium itaconate.

Processes of preparing metal salts of unsaturated carboxylic acids are well known in the art, and many of these compounds are commercially available. For example, the metal salt of an unsaturated carboxylic acid may be prepared by adding an unsaturated carboxylic acid dropwise to a solution of NaOEt in ethanol while maintaining the temperature below 25° C. and then stirring for one hour.

The haloorganoalkoxysilane has the formula $XR^3Si(OR^4)_n R^5_{3-n}$ (II), where X is halo, $R^3$ is $C_1$-$C_6$ hydrocarbylene, each $R^4$ is independently $C_1$-$C_{10}$ hydrocarbyl, each $R^5$ is independently H or $C_1$-$C_6$ hydrocarbyl, and n is 1, 2 or 3. Examples of halo atoms represented by X include —F, —Cl, —Br, and —I.

The hydrocarbylene groups represented by $R^3$ typically have from 1 to 6 carbon atoms, alternatively from 2 to 4 carbon atoms, alternatively 3 carbon atoms. Hydrocarbylene groups containing at least three carbon atoms can have a branched or unbranched structure. Examples of hydrocarbylene groups include, but are not limited to, methylene, ethylene, propylene, 1-methylethylene, butylene, 1-methylpropylene, 2-methylpropylene, 1,1-dimethylethylene, pentylene, 1-methylbutylene, 1-ethylpropylene, 2-methylbutylene, 3-methylbutylene, 1,2-dimethylpropylene, 2,2-dimethylpropylene, hexylene, or a similar hydrocarbylene group.

The hydrocarbyl groups represented by $R^4$ typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$ above and alkyl, such as hexyl, heptyl, octyl, nonyl, and decyl; cycloalkyl, such as methylcyclohexyl; aryl, such as napthyl; alkaryl such as tolyl and xylyl; aralkyl, such as benzyl and phenylethyl; and aralkenyl, such as styryl and cinnamyl.

The hydrocarbyl groups represented by $R^5$ typically have from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$.

Examples of the haloorganoalkoxysilane of formula (II) include, but are not limited to, chloromethyldimethylmethoxysilane, chloromethyltrimethoxysilane, chloromethyltriethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, 3-chloropropylethyldimethoxysilane, 3-chloropropylethyldiethoxysilane, 3-bromopropyltrimethoxysilane, 3-bromopropyltriethoxysilane, 3-iodopropyltrimethoxysilane, 3-iodopropyltriethoxysilane. In one embodiment, the haloorganoalkoxysilane of formula (II) is 3-chloropropyltrimethoxy silane or 3-chloropropyltriethoxysilane.

Processes of preparing haloorganoalkoxysilanes are well known in the art; many of these compounds are commercially available.

The mineral spirits are typically petroleum distillates comprising a mixture of isoalkanes, alkanes, and cycloalkanes. The mineral spirits typically comprise isoalkanes having from 8 to 16 carbon atoms, alternatively from 10 to 14 carbon atoms, alternatively from 10 to 13 carbon atoms, alternatively from 11 to 13 carbon atoms. An example of mineral spirits includes, but is not limited to, tetrapropane, which is assigned CAS 68551-17-7 and which comprises isoalkanes having from 10 to 13 carbon atoms. Mineral spirits are made by processes well known in the art and are available commercially.

The phase-transfer catalyst is any phase-transfer catalyst known to function as a solid-solution phase-transfer catalyst in the nucleophilic substitution reaction between a metal salt of an unsaturated carboxylic acid and a haloorganoalkoxysilane to form an acryloyloxysilane.

Examples of the phase-transfer catalyst include, but are not limited to, amines, such as triethylamine, dimethylaniline, 1,8-diazabicyclo[5.4.0]undec-7-ene, 1,4-diazabicyclo[2.2.2]octane, and 1,5-diazabicyclo[4.3.0]-non-5-ene; quaternary ammonium compounds, such as tributylmethyl ammonium chloride, triethylcetyl ammonium bromide, didodecyl dimethyl ammonium chloride, distearyl dimethyl ammonium chloride, tricaprylmethyl ammonium chloride, ALIQUAT® 336 [tris(n-$C_8$- and $C_{10}$-alkyl)methyl ammonium chloride], trioctyl methyl ammonium chloride, or tetrabutyl ammonium chloride or bromide; and quaternary phosphonium compounds, such as tetra-n-butylphosphonium bromide, tetra-n-butylphosphonium chloride, methyltri-n-butylphosphonium chloride, methyltri-n-butylphosphonium bromide, n-butyltriphenylphosphonium bromide, n-butyltriphenylphosphonium bromide, n-butyltriphenylphosphonium chloride, methyltriphenylphosphonium chloride and methyltriphenylphosphonium bromide. In one embodiment, the phase-transfer catalyst is tetrabutyl ammonium chloride or bromide, methyltriphenylphosphonium chloride, n-butyltriphenylphosphonium bromide, or tetra-n-butylphosphonium bromide.

The phase-transfer catalysts are made by processes known in the art. Many of these compounds are available commercially.

The first process of the invention may, optionally, be carried out in the presence of one or more free-radical inhibitors. As used herein, "inhibitors" are compounds that inhibit free-radical polymerization reactions.

Examples of inhibitors include, but are not limited to, amines, such as ethylenediaminetetraacetic acid, aromatic amines, such as N,N'-p-phenylenediamine, N,N'-di-β-naphthyl-p-phenylenediamine, and phenothiazine, quinines, hydroquinones, such as hydroquinone monomethyl ether, sterically hindered phenols, such as 2,6-di-tertbutylphenol, 2,6-di-tert-butyl-4-methylphenol, 2,6-di-tert-butyl-4-(N,N-dimethylamino)methylphenol, and butylated hydroxytoluene, and stable free radicals.

The inhibitors are made by processes known in the art. Many of these inhibitors are available commercially.

The reactor for the first process of the invention can be any suitable reactor for reacting a metal salt of an unsaturated carboxylic acid with a haloorganoalkoxysilane in the presences of a phase-transfer catalyst. For example, a glass, round-bottom flask may be used.

The reactants may be combined in any order, but, typically, the metal salt of the unsaturated carboxylic acid is added to the reactor, or produced in the reactor as described above, followed by the addition of any inhibitors, the phase-transfer catalyst, the mineral spirits, and the haloorganoalkoxysilane.

The rate of addition of the reactants in the first process is not critical.

The reaction of the first process is typically carried out at a temperature of from 50 to 160° C., alternatively from 80 to 140° C., alternatively from 110 to 130° C., and at a pressure from 0 to 1000 kPag, alternatively from 50 to 200 kPag, alternatively from 80 to 150 kPag. The reactants are typically combined as described above at ambient temperature and then the combination brought to the temperatures and pressures described above.

The reaction of the first process of the invention is typically carried out until at least 50% (w/w) of the haloorganoalkoxysilane has reacted, alternatively until at least 80% of the haloorganoalkoxysilane has reacted, alternatively until from 90 to 100% of the haloorganoalkoxysilane has reacted. The progression of the reaction of the haloorganoalkoxysilane can be monitored by standard processes known in the art, for example by gas chromatography (GC).

Typically, the time required to carry out the reaction of the first process is at least 30 minutes, alternatively from 60 to 6000 minutes, alternatively from 120 to 300 minutes.

The molar ratio of the metal salt of the unsaturated carboxylic acid to the haloorganoalkoxysilane is typically from 0.5-1.5:1, alternatively from 0.9-1.1:1, alternatively from 1-1.05:1.

The mineral spirits are typically combined at from 10 to 90% (w/w), alternatively 20 to 80% (w/w), alternatively from 30 to 60% (w/w), based upon the combined weight of the mineral spirits, the haloorganoalkoxysilane, and the salt of unsaturated carboxylic acid.

The phase-transfer catalyst is in a catalytic effective amount. As used herein, a "catalytic effective amount" is an amount that will catalyze the nucleophilic substitution reaction between the haloorganoalkoxysilane and the salt of an unsaturated carboxylic acid to produce an acryloyloxysilane. For example, a catalytic effective amount is at least 0.001% (w/w), alternatively from 0.005 to 0.5%, alternatively from 0.01 to 0.05% (w/w), based on the combined weight of the phase-transfer catalysts, the haloorganoalkoxysilane, the salt of an unsaturated carboxylic acid, and the mineral spirits.

When included, the inhibitor is typically from 1 to 10,000 ppmw, alternatively from 10 to 1000 ppmw, based on the combined weight of the inhibitor, the haloorganoalkoxysilane, the metal salt of the unsaturated carboxylic acid, and the mineral spirits.

The reaction of the first process of the invention is typically carried out in an inert gas atmosphere; however, it may be carried out in air. The inert gas is a gas that is unreactive toward the components present in the reaction mixture under reaction conditions. Examples of inert gases are nitrogen and argon.

The reaction of the first process of the invention typically carried out in, substantially, the absence of water. For example, the water is typically below 10,000 ppmw, based on the combined weight of the water, the haloorganoalkoxysilane, the metal salt of the unsaturated carboxylic acid, and the mineral spirits. The absence of water is accomplished by customary processes of removing traces of water from the components present in the reaction vessel. For example, the components may be dried through the aid of a drying agent. One skilled in the art would know suitable drying agents.

The reaction forms a mixture comprising an acryloyloxysilane, and a metal halide having the formula $M^{a+}X^-_a$ (III), wherein $X^-$ is a halide anion.

The acryloyloxysilane has the formula $CR^6_2$=$CR^1COOR^3Si(OR^4)_nR^5_{3-n}$ (IV), wherein each $R^1$, $R^3$, $R^4$, $R^5$, and n is independently as described above for the haloorganoalkoxysilane and the metal salt of a carboxylic acid, and each $R^6$ is independently H, $C_1$-$C_6$ hydrocarbyl, or $COOR^3Si(OR^4)_nR^5_{3-n}$, wherein each $R^3$, $R^4$, $R^5$, and n is independently as described above for the haloorganoalkoxysilane and the metal salt of a carboxylic acid.

Examples of the acryloyloxysilane include, but are not limited to, methacryloyloxymethyldimethylmethoxysilane, γ-methacryloyloxypropylmethydimethoxysilane, γ-methacryloyloxypropyltrimethoxysilane, γ-methacryloyloxypropyltriethoxysilane, γ-methacryloyloxybutyldimethoxysilane, δ-methacryloyloxybutyltrimethoxysilane, δ-methacryloyloxybutylmethyldimethoxysilane, acryloyloxymethyldimethylmethoxysilane, γ-acryloyloxypropylmethyldimethoxysilane, γ-acryloyloxypropyltrimethoxysilane, γ-acryloyloxypropyltriethoxysilane, γ-acryloyloxypropylbutyldimethoxysilane, δ-acryloyloxybutyltrimethoxysilane, δ-acryloyloxybutylmethyldimethoxysilane, bis(γ-trimethoxysilylpropyl)fumarate, bis(γ-triethoxysilylpropyl)fumarate, bis(γ-trimethoxysilylpropyl)maleate, bis(γ-triethoxysilylpropyl)maleate, bis(γ-trimethoxysilylpropyl)itaconate, bis(γ-triethoxysilylpropyl)itaconate.

The metal halide is according to the formula $M^{a+}X^-_a$ (III), wherein M and a are as defined and exemplified above for the metal salt of the unsaturated carboxylic acid, and $X^-$ is a halide anion. Examples of halide anions include chloride, bromide, fluoride and iodide. Examples of the metal halide include, but are not limited to sodium chloride, sodium bromide, sodium iodide, potassium chloride, potassium bromide, potassium iodide, magnesium chloride, magnesium bromide, magnesium iodide, calcium chloride, calcium bromide, and calcium iodide.

The first process of the invention may also comprise removing at least a portion of the first metal halide from the mixture. As used herein, "a portion" means enough to reduce the metal halide in the acryloyloxysilane to within the ranges described below. For example, a portion is typically at least 50%, alternatively at least 90%, alternatively at least 99.99%, of the initial amount of the metal halide in the mixture.

The metal halide may be removed from the mixture by processes known in the art for removing a solid metal halide from an organic material. The metal halide may be removed by, for example, filtration, decantation, washing, or a combination of filtration, decantation and washing. In one embodiment, the metal halide is removed by filtration or decantation. In another embodiment, the metal halide is removed by decanting the acryloyloxysilane from the metal halide followed by washing, as described and exemplified below in the second process of the invention, the metal halide with a brine solution.

After the step of removing at least a portion of the metal halide from the mixture, the acryloyloxysilane typically has less than 10,000 parts per million by weight (ppmw), alternatively from 1 to 1000 ppmw, alternatively from 10 to 100 ppmw, based on the weight of the acryloyloxysilane, of the first metal halide.

The first process of the invention may further comprise recovering the acryloyloxysilane. The recovering may be accomplished by processes known in the art, for example by distillation.

The first process of the present invention produces an acryloyloxysilane. Further, the first process of the present invention produces a metal halide precipitate that has coarse particles that require less time to filter. Still further, the first process of the present invention produces a metal halide precipitate that settles quickly forming a distinct layer enabling efficient separation of the acryloyloxysilane from the metal halide by decantation.

The second process of the invention involves a method of purifying an acryloyloxysilane, the method comprising washing a mixture comprising an acryloyloxysilane, a first metal halide, and a non-polar solvent with a solution comprising water and, optionally, a second metal halide, to produce an organic phase comprising the acryloyloxysilane and an aqueous phase comprising at least a portion of the first metal halide.

The acryloyloxysilane of the second process is as described and exemplified above for the first process of the invention.

The non-polar solvent has a dielectric constant below 10, alternatively below 5, alternatively from 1 to 5.

The non-polar solvent of the second process has a density less than 1.0 grams per milliliter (g/mL), alternatively from 0.6 to 0.9 grams per mL, alternatively from 0.7 to 0.8 g/mL, at 25° C.

Examples of the non-polar solvents include, but are not limited to, organic solvents such as mineral spirits, toluene, m-, o-, and p-xylene and mixtures thereof, n-pentane, n-hexane, n-heptane, cyclopentane, cyclohexane, cyclooctane, cyclohexane, cis-cyclooctene, tert-butyl methyl ether and di-n-butyl ether. In one embodiment, the non-polar solvent is mineral spirits as defined and exemplified above for the first process of the invention.

The first metal halide of the second process is according to the formula (III) as described and exemplified above for the metal halide of the first process.

The mixture of the second process of the invention may be formed according to the reaction of the first process of the invention, as described and exemplified above, with the non-polar solvent described substituted for the mineral spirits. For example, the mixture may be formed by reacting a metal salt of an unsaturated carboxylic acid with a haloorganoalkoxysilane in the presence of a non-polar solvent and a catalytic effective amount of a phase-transfer catalyst, wherein the non-polar solvent is as described and exemplified above, and wherein the metal salt of an unsaturated carboxylic acid, the haloorganoalkoxysilane, the phase-transfer catalyst, the reactor, and the reaction conditions are as described and exemplified above for the reaction of the first process of the invention.

The mixture may also be formed by combining the non-polar solvent with the acryloyloxysilane and the first metal halide in the reactors and with the conditions typically used for blending solutions. For example, the combining may be done at ambient temperatures in a mixing tank with a mixing blade.

The acryloyloxysilane is typically present in the mixture of the second process of the invention at from 1 to 90% (w/w), alternatively from 10 to 80%, alternatively from 30 to 70%, based upon the combined weight of the non-polar solvent, the acryloyloxysilane, and the first metal halide.

The non-polar solvent is present in the mixture of the second process of the invention at from 10 to 90% (w/w), alternatively 15 to 80% (w/w), alternatively from 25 to 60% (w/w), based upon the combined weight of the non-polar solvent, the acryloyloxysilane, and the first metal halide.

The first metal halide is typically present in the mixture of the second process of the invention at from 1 to 50% (w/w), alternatively from 5 to 30% (w/w), alternatively from 5 to 15% (w/w), based on the combined weight of the acryloyloxysilane, the non-polar solvent, and the first metal halide. The amount of the first metal halide in the mixture may be calculated stoichiometrically or determined by processes known in the art for determining the amount of a metal halide in a mixture, for example by ion chromatography.

The solution in the second process of the invention comprises water and, optionally, a second metal halide. For example, the solution may comprise from 0% to a less than a saturated concentration, alternatively from 0% to 50% (w/w), alternatively from 0 to 15% (w/w), based on the combined weight of the second metal halide and the water, of a second metal halide. As used herein, a "saturated concentration" means the concentration, at a particular temperature and pressure, at which no additional amount of the second metal halide will dissolve.

The water is typically deionized water; however, other types of water, such as distilled or tap water, may be used.

The second metal halide is as described and exemplified above for the first metal halide of the second process of the invention.

The second metal halide may be the same or different as the first metal halide and may be a mixture of metal halides, each according to the formula (III) above. In one embodiment, the second metal halide is the same as the first metal halide and is potassium or sodium chloride.

Examples of solutions useful in the second process of the invention include water and less than saturated aqueous solutions of sodium chloride, sodium bromide, potassium chloride, or potassium bromide.

When the solution comprises the second metal halide, the solution may be made by processes known in the art for making such solutions. Many aqueous solutions of metal halides are available commercially.

The second process of the invention may be conducted in any vessel known in the art for washing an organic solution with water. For example, step (ii) may be conducted in a stainless steel tank equipped with mechanical mixing.

The time required for the second process of the invention is equal to the time required to combine and mix the solution and the mixture and for the solution to extract the first metal halide from the mixture. For example, the time of required for the second process of the invention is typically from 1 minute to 60 minutes, alternatively from 5 minutes to 45 minutes, alternatively from 10 minutes to 45 minutes.

The order and rate of addition of the solution and the mixture in the second process of the invention is generally not critical. Typically the solution and mixture may be added at any rate and in any order.

The temperature at which the second process of the invention is conducted is typically from 0 to 120° C., alternatively from 0 to 60° C., alternatively from 10 to 40° C.

The pressure of the second process of the invention is typically from sub-atmospheric to super-atmospheric pressures, alternatively from 0 to 1000 kPag, alternatively from 0 to 100 kPag, alternatively at atmospheric pressure.

The mixture in the second process is washed with a sufficient amount of the solution so the first metal halide and the second metal halide together are at least 15% (w/w), alternatively at least 18%, alternatively from 18 to 50% of the combined weight of the first metal halide, the second metal halide, and the water. As used herein, a "sufficient amount" is an amount that is not too great to cause the combined percentage of the first and second metal halide to be outside the prescribed limits. A sufficient amount of the solution may be calculated from the weight of the first metal halide in the mixture and the second metal halide and water in the solution, which may be determined using processes known in the art, for example by ion chromatography.

The washing of the second process produces an organic phase, comprising the acryloyloxysilane and the non-polar solvent, and an aqueous phase, comprising the solution and at least a portion of the first metal halide. The organic and aqueous phases are immiscible.

The aqueous phase comprises at least 15%, alternatively at least 18%, alternatively from 18% to a saturated concentration, based on the weight of the first metal halide, the second metal halide, and the water, of the first metal halide and second metal halide combined.

The second process of the invention may further comprise the step of recovering the acryloyloxysilane. The recovering may be accomplished by processes known in the art. For example, the organic phase and the aqueous phase may be separated using known processes, such as by decantation, followed by distillation of the organic phase.

After washing in the second process of the invention, the acryloyloxysilane typically comprises less than 10,000 parts per million by weight (ppmw), alternatively from 1 to 1000 ppmw, alternatively from 10 to 100 ppmw, based on the weight of the acryloyloxysilane, of the first metal halide.

The second process of the invention provides fast separation of the acryloyloxysilane and metal halide. Further, the second process of the invention eliminates the need for the filtration of the organic phase. Still further, the second process allows for washing the acryloyloxysilane without significant hydrolysis and without formation of a dispersion that is hard to separate.

The acryloyloxysilane of the first and second process of the invention may be used as a coupling agent for unsaturated resin or polymer systems, an adhesion promoter at organic-inorganic interfaces, and as a surface modifier

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 1

List of abbreviations used in the examples.

| Abbreviation | Word |
|---|---|
| g | gram |
| Me | methyl |
| wt | weight |
| % | percent |
| mol | mole |
| mmol | millimole |
| hr | hour |
| ° C. | degrees Celsius |
| NA | Not Applicable |
| mL | milliliters |
| solids content | (wt. of dried sample/wt. of initial sample) × 100 and determined as described below |
| rpm | revolutions per minute |
| ppmw | parts per million by weight |
| PTZ | Phenothiazine |

TABLE 1-continued

List of abbreviations used in the examples.

| Abbreviation | Word |
|---|---|
| BHT | butylated hydroxytoluene |
| NaOEt | sodium ethoxylate |
| TBAB | tetrabutylammonium bromide |
| DBU | 1,8-diazabicyclo[5.4.0]undec-7-ene |
| CPTES | γ-chloropropyltriethoxysilane |
| g-ATE | γ-acryloyloxypropyltriethoxysilane |
| yield | (isolated wt. of organoalkoxysilane product/theoretical wt. of organoalkoxysilane product) × 100 |
| PTC | Phase-transfer catalysis |
| EDTA-NA | ethylenediaminetetraacetic acid disodium salt |
| CPTMS | γ-chloropropyltrimethoxysilane |
| g-ATM | γ-acryloyloxypropyltrimethoxysilane |
| % organic recovery rate | (isolated organics/theoretical weight of organics) × 100 |
| organics | organoalkoxysilane product and non-polar solvent |

Example 1

A 500 ml three-neck round bottom flask equipped with a mechanical agitator and a thermometer was loaded with 72.5 g of a 21% (w/w) NaOEt solution in ethanol. Acrylic acid (16.6 g; 231 mmol) was added dropwise while the temperature was maintained below 25° C. After the acrylic acid addition, the slurry was agitated for 1 hr at ambient temperature. Then the stabilizers PTZ and BHT (0.022 g each), TBAB (2.98 g; 9.24 mmol), CPTES (55.6 g; 231 mmol) and mineral spirits (55.6 g) (CAS 68551-17-7; $C_{10-13}$ isoalkanes) were sequentially added to the flask. The temperature of the reaction mixture was gradually raised up to 140° C. while the low boilers (65.5 g) were condensed and collected through distillation. The reaction mixture was heated at 140° C. for 3 hr giving approximately 9% (w/w) sodium chloride in the reaction mixture. GC analysis showed 95% conversion to g-ATE.

Agitation was ceased and the sodium chloride salt precipitated quickly and completely settled to give a clean interface between the sodium chloride cake and the supernatant. The supernatant (70.4 g) was decanted. Then 68.9 g of 15% (w/w) brine was added to the sodium chloride cake to give a combined weight percent of metal halide in water of about 30%. After mixing to dissolve the sodium chloride and bodying to allow phase separation, the organic phase (35.1 g) was separated through decantation. This sodium chloride separation was completed in less than 1 hr. The combined crude product (105.5 g) was subject to vacuum distillation. The mineral spirits were removed as low boilers. The final g-ATE product (42.6 g) with a purity of 98.0% (w/w) was isolated in 67% yield. This example shows the speed and ease that the metal halide may be removed from g-ATE using the process of the invention.

Comparative Example 1

A 250 ml three-neck round bottom flask equipped with a mechanical agitator and a thermometer was loaded with 94.2 g (21% (w/w)) NaOEt solution in ethanol. Acrylic acid (22.6 g; 314 mmol) was added dropwise while the temperature was maintained below 25° C. After the addition, the slurry was agitated for 1 hr at the ambient temperature. Then the stabilizers PTZ and BHT (0.031 g each), TBAB (2.02 g; 6.27 mmol) and CPTES (75.52 g; 314 mmol) were added sequentially. The temperature of the reaction mixture was gradually raised up to 140° C. while the low boilers (82.7 g) were condensed and collected through simple distillation. During the distillation, the reaction mixture became very viscous causing agitation difficulty. The viscosity dropped when the PTC reaction started to near 140° C. The reaction mixture was heated at 140° C. for 3 hr. GC analysis suggested 89% conversion to g-ATE. Filtration of the sodium chloride by-product took more than 10 hr. This example shows the long times required for filtration of the metal halide not according to the invention.

Example 2

Acrylic acid (15.7 kg) was added to a pre-mix of 70 kg of 21% (w/w) sodium ethoxide solution in ethanol, 61.2 kg of xylene and 30 g of PTZ, BHT and EDTA-NA. Then 1.2 kg of TBAB and 53 kg of CPTES were added. After ethanol was distilled, the reaction mixture was heated at 120° C. for 5 hours giving approximately 9% (w/w) sodium chloride in the reaction mixture.

Water (88.4 g) was poured into 221.0 g of the suspension reaction mixture to give a combined weight percent of sodium chloride in water of about 18%. After a brief agitation, the mixture separated into a hazy organic phase and a cloudy salt suspension. A clean solution-solution interface was formed in 3 minutes, and 191.6 g of organics were decanted, resulting in an 86% organic recovery rate. GC of the organics showed no noticeable compositional difference before and after the water wash indicating no appreciable hydrolysis of g-ATE. This example shows that the metal halide may be removed from g-ATE by washing without hydrolysis of the g-ATE.

Comparative Example 2

37.0 g of the g-ATE suspension reaction mixture from example 2 was centrifuged at 5900 rpm for 10 minutes. The mixture separated into a clear organic phase and a dense sodium chloride cake. 25.1 g of organics were decanted, resulting in a 68% organic recovery rate. This example shows the lower yields experience with centrifuging rather than washing.

Example 3

Acrylic acid (23.4 kg) was added to a pre-mix of 70.1 kg of 25% (w/w) sodium methoxide solution in methanol, 38.7 kg of xylene and 50 g each of PTZ, BHT and EDTA-NA. Then 1.5 kg of TBAB and 66.0 kg of CPTMS were added. After methanol was distilled, the reaction mixture was heated at 120° C. for 5 hours to create a suspension reaction mixture containing approximately 14% (w/w) sodium chloride.

81 g of water were poured into 202.6 g of the suspension reaction mixture to give a combined weight percent of metal halide in water of about 26%. After a brief agitation, the mixture separated into a hazy organic phase and a cloudy sodium chloride suspension. A clean solution-solution interface was formed in 3 minutes. 153.6 g of organics were decanted, resulting in a 76% organic recovery rate. GC of the organics showed no noticeable compositional difference before and after the wash indicating no appreciable hydrolysis. This example shows that washing allows for quick separation of the metal halide by-product for the product with no appreciable hydrolysis of the product.

Comparative Example 3

40.5 g of the g-ATM suspension reaction mixture from example 3 was centrifuged at 5900 rpm for 10 minutes. The mixture separated into a clear organic phase and a dense sodium chloride cake. 24.0 g of organics were decanted, resulting in a 59% organic recovery rate. This example shows the low yields when centrifuging is used as the method of separating the metal halide from the product compared to the method of example 3.

Example 4

10 kg of potassium sorbate, 10 kg of toluene, 12.7 kg of CPTMS, 25 g of PTZ, BHT and EDTA-NA each, and 500 g of TBAB were mixed in a 50 L reactor. The reaction mixture was heated at 115° C. for 5 hours forming a suspension reaction mixture containing approximately 13% (w/w) KCl. 97.8 g of water were poured into 342.5 g of the suspension reaction mixture to give a combined weight percent of metal halide in water of about 31%. After a brief agitation, the mixture separated into a hazy organic phase and a KCl suspension. A clean solution-solution interface was formed in 3 minutes. 247.1 g of organics were decanted, resulting in a 72% organic recovery rate. GC of the organics showed no noticeable compositional difference before and after the water wash indicating no appreciable hydrolysis. This example shows that the process works with unsaturated organoalkoxysilanes containing sorboxy groups with good yield and quick separation of the metal halide.

Example 5

Disodium fumarate (93.0 g; 0.581 mol), CPTES (280.0 g; 1.16 mol), PTZ and BHT (0.112 g/each) and DBU (3.52 g) were sequentially added to a 500 ml round bottom flask equipped with a mechanical agitator. The reaction mixture was heated at 140° C. for 18 hr. After bodying for 2 days, 191.3 g of clear brownish supernatant was decanted. Then 180 ml of hexanes was added to the salt residue to form a slurry. After forming the slurry, 480 g of 15% brine was added and mixed. After 30 min settlement, 224.5 g of clear organics were separated and vacuum stripped to give 82.6 g of a clear brownish liquid with low volatility. The two clear brownish liquids were combined and subject to a simple distillation under vacuum (less than 1 torr) at 140° C. The bis(triethoxysilylpropyl)fumarate product (238.3 g) was isolated in 92% yield. This example shows the speed and ease that the metal halide may be removed from bis(triethoxysilylpropyl)fumarate using the process of the invention.

That which is claimed is:

1. A process for preparing an acryloyloxysilane, the process comprising: reacting a metal salt of a carboxylic acid having the formula $[CR^2_2=CR^1COO^-]_a\text{-}M^{a+}$ (I), with a haloorganoalkoxysilane having the formula $XR^3Si(OR^4)_n R^5_{3-n}$ (II) in the presence of mineral spirits, wherein the mineral spirits are petroleum distillates comprising a mixture of isoalkane, alkane, and cycloalkane, and a phase transfer catalyst at a temperature of from 50 to 160° C. to form a mixture comprising an acryloyloxysilane and a metal halide having the formula $M^{a+}X^-_a$ (III), wherein $R^1$ is H or $C_1$-$C_6$ hydrocarbyl, each $R^2$ is independently $R^1$ or $[COO^-]_a M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

2. The process of claim 1, wherein the acryloyloxysilane has the formula $CR^6_2=CR^1COOR^3Si(OR^4)_n R^5_{3-n}$ (IV), wherein $R^1$, $R^3$, $R^4$, $R^5$, and n are as defined in claim 1, and wherein each $R^6$ is independently H, $C_1$-$C_6$ hydrocarbyl, or $COOR^3Si(OR^4)_n R^5_{3-n}$, wherein $R^3$, $R^4$, $R^5$, and n are as defined in claim 1.

3. The process of claim 1, further comprising at least one of the following steps or limitations a) through e)
   a) removing at least a portion of the metal halide from the mixture by filtration, decantation, or centrifugation and decantation wherein the mineral spirits are from 30 to 60% (w/w);
   b) wherein $M^{a+}$ is a sodium ion or potassium ion, a is 1, and X is chloro;
   c) wherein each $R^1$ is independently H, methyl, or $[CH_2COO^-]M^{a+}$, each $R^2$ is independently H, methyl, or $[COO^+]_aM^{a+}$, $R^3$ is methylene, ethylene, or propylene, each $R^4$ is independently methyl or ethyl, each $R^5$ is independently H, methyl, or ethyl, and n is 3;
   d) wherein the phase-transfer catalyst is tetrabutylammonium bromide;
   e) recovering the acryloyloxysilane.

4. The process of claim 1, wherein the metal salt of a carboxylic acid is selected from a metal salt of fumaric acid or a metal salt of acrylic acid.

5. The process of claim 4 wherein the acryloyloxysilane is γ-acryloyloxypropylmethyldimethoxysilane, γ-acryloyloxypropyltrimethoxysilane, γ-acryloyloxypropyltriethoxysilane, bis(γ-trimethoxysilylpropyl) fumarate, or bis(γ-triethoxysilylpropyl) fumarate.

6. The process of claim 1, further comprising washing the mixture comprising an acryloyloxysilane, a first metal halide, and a non-polar solvent with a solution comprising water and, optionally, a second metal halide, to produce an organic phase comprising the acryloyloxysilane and an aqueous phase comprising at least a portion of the first metal halide.

7. The process of claim 6, wherein the acryloyloxysilane has the formula $CR^6{}_2=CR^1COOR^3Si(OR^4)_nR^5{}_{3-n}$ (IV), wherein $R^1$ is H or $C_1$-$C_6$ hydrocarbyl, $R^3$ is $C_1$-$C_6$ hydrocarbylene, each $R^4$ is independently $C_1$-$C_{10}$ hydrocarbyl, each $R^5$ is independently H or $C_1$-$C_6$ hydrocarbyl, each $R^6$ is independently H, $C_1$-$C_6$ hydrocarbyl, or $-COOR^3Si(OR^4)_nR^5{}_{3-n}$, wherein $R^3$, $R^4$, and $R^5$ are as defined above, and n is an integer from 1 to 3.

8. The process of claim 6, wherein the non-polar solvent is from 10 to 90% (w/w).

9. The process of claim 6, where the first metal halide and second metal halide are according to the formula $M^{a+}X^-_a$ (III), wherein $M^{a+}$ is an alkali metal cation or alkaline earth metal cation, X is halo, and a is 1 or 2.

10. The process of claim 6, wherein the solution comprises from 0% to a less than saturated concentration of a second metal halide.

11. The process of claim 6, wherein the mixture is washed with a sufficient amount of the solution so the first metal halide and the second metal halide together are at least 15% (w/w) of the combined weight of the first metal halide, the second metal halide, and the water.

12. The process of claim 6 further comprising forming the mixture by reacting a metal salt of a carboxylic acid having the formula $[CR^2{}_2=CR^1COO^-]_aM^{a+}$ (I), with a haloorganoalkoxysilane having the formula $XR^3Si(OR^4)_nR^5{}_{3-n}$ (II) in the presence of the non-polar solvent and a phase transfer catalyst at a temperature of from 50 to 160° C. to form a mixture comprising an acryloyloxysilane and a metal halide having the formula $M^{a+}X^-_a$ (III), wherein each $R^1$ is independently H or $C_1$-$C_6$ hydrocarbyl, each $R^2$ is independently $R^1$ or $[COO^-]_aM^{a+}$, $R^3$ is $C_1$-$C_6$ hydrocarbylene, each $R^4$ is independently $C_1$-$C_{10}$ hydrocarbyl, each $R^5$ is independently $R^1$, each $M^{a+}$ is an alkali metal cation or alkaline earth metal cation, a is 1 or 2, X is halo, and n is an integer from 1 to 3.

13. The process of claim 12, wherein each $R^2$ is independently H, methyl, or $[COO^-]_aM^{a+}$, $R^1$ is H or methyl, $R^3$ is methylene, ethylene, or propylene, $R^4$ is methyl, ethyl or propyl, $R^5$ is H, methyl, or ethyl, X is chloro, and n is 2 or 3.

14. The process of claim 12, wherein $M^{a+}$ is a potassium cation or a sodium cation, X is chloride, and a is 1.

15. The process of claim 12, wherein the phase-transfer catalyst is tetrabutylammonium bromide.

16. The process of claim 6, wherein the mixture comprises from 30 to 60% (w/w) of the non-polar solvent, and wherein the non-polar solvent has a density of less than 1.0 g/ml and a dielectric constant below 10.

17. The process of claim 6, wherein the non-polar solvent is mineral spirits.

18. The process of claim 6, wherein the first metal halide and second metal halide are the same.

19. The process of claim 6, wherein the mixture comprises from 5 to 15% (w/w) of the first metal halide.

20. The process of claim 6, further comprising recovering the acryloyloxysilane.

* * * * *